US006297405B1

(12) United States Patent
Anderson et al.

(10) Patent No.: US 6,297,405 B1
(45) Date of Patent: Oct. 2, 2001

(54) FLUORINATED AND CHLORINATED BENZALDEHYDES

(75) Inventors: John David O. Anderson, Moore; Walter Scrivens, Newberry, both of SC (US)

(73) Assignee: Milliken & Company, Spartanburg, SC (US)

( * ) Notice: Subject to any disclaimer, the term of this patent is extended or adjusted under 35 U.S.C. 154(b) by 0 days.

(21) Appl. No.: 09/653,937

(22) Filed: Sep. 1, 2000

(51) Int. Cl.[7] .......................... C07C 47/52; C07C 47/54; C07C 17/20; C07C 19/08
(52) U.S. Cl. .................. 568/425; 568/428; 568/435; 570/127; 570/170
(58) Field of Search .................................. 568/425, 428, 568/435; 570/127, 170

(56) References Cited

U.S. PATENT DOCUMENTS

| | | | |
|---|---|---|---|
| 4,622,429 | * 11/1986 | Blank et al. | |
| 4,808,650 | 2/1989 | Titus et al. | 524/108 |
| 4,902,807 | 2/1990 | Kobayashi et al. | 549/364 |
| 5,106,999 | 4/1992 | Gardlik et al. | 549/364 |
| 5,138,099 | * 8/1992 | Lang. | |
| 5,696,186 | 12/1997 | Videau | 524/48 |

FOREIGN PATENT DOCUMENTS

2077255 A   12/1981   (GB).

OTHER PUBLICATIONS

Aldrich. Catalog Handbook of Fine Chemicals. 1996–1997 (catalog #29, 233–8; p 1447).*

* cited by examiner

Primary Examiner—Johann Richter
Assistant Examiner—Sikarl A. Witherspoon
(74) Attorney, Agent, or Firm—Terry T. Moyer; William S. Parks

(57) ABSTRACT

A process for the preparation of aromatic aldehydes containing fluorine, and more particularly, to a formylation process for fluorinated aromatic derivatives through the reaction of fluorinated benzenes with carbon monoxide and aluminum chloride at a relatively low pressure, a low temperature, and in the presence of at most a catalytic amount of an acid (such as aqueous hydrochloric acid) is herein disclosed. The resultant fluorinated benzaldehydes are useful as precursors to the formation of a number of different compounds, such as dyestuffs, flavorings, fragrances, herbicidal compounds, nucleating agents, polymer additives, and the like. The inventive method provides a very cost effective and safe procedure for producing such fluorinated benzaldehydes in very high yields. The particular novel multi-substituted benzaldehydes are also encompassed within this invention.

17 Claims, No Drawings

FLUORINATED AND CHLORINATED BENZALDEHYDES

FIELD OF THE INVENTION

The present invention relates to a process for the preparation of aromatic aldehydes containing fluorine, and more particularly, to a formylation process for fluorinated aromatic derivatives through the reaction of fluorinated benzenes with carbon monoxide and aluminum chloride at a relatively low pressure, a low temperature, and in the presence of at most a catalytic amount of an acid (such as aqueous hydrochloric acid). The resultant fluorinated benzaldehydes are useful as precursors to the formation of a number of different compounds, such as dyestuffs, flavorings, fragrances, herbicidal compounds, nucleating agents, polymer additives, and the like. The inventive method provides a very cost effective and safe procedure for producing such fluorinated benzaldehydes in very high yields. The particular novel multi-substituted benzaldehydes are also encompassed within this invention.

BACKGROUND OF THE INVENTION

Aromatic aldehydes are prepared by two primary synthetic methods: a direct method which consists of attaching a CHO group onto an aromatic derivative, and an indirect method which consists of oxidizing a group which is already present on the aromatic derivative. There are several well known methods for electrophilically formylating aromatic compounds containing activating (electron-donating) substituents, but these fail completely or are impractical for aromatic compounds which contain electron withdrawing substituents such as fluorine. To overcome this dilemma, new synthetic processes are continually being developed.

A direct formylation method is disclosed within U.S. Pat. No. 4,588,844 to Kysela et al., which describes a reaction between an aromatic compound and urotropine (hexamethylenetetramine, HMT) in a hydrofluoric acid medium. Yields obtained for compounds such as fluorobenzene were rather low (about 30%) and are not suitable for industrial utilization.

Another direct formylation method is disclosed within by U.S. Pat. No. 5,068,450 to Crochemore et al., which discloses a process consisting of reacting methyl formate with an aromatic derivative in liquid hydrofluoric acid in the presence of boron trifluoride. Yields of fluorobenzaldehyde obtained by incorporating fluorobenzene in this process are high (about 85%) and reportedly give a single isomer, 4-fluorobenzaldehyde.

U.S. Pat. No. 5,138,099 to Lang also discloses a direct formylation procedure in which a fluorinated aromatic derivative (fluorobenzene, 2-fluorotoluene) is reacted with dichloromethyl methyl ether in methylene chloride in the presence of ferric chloride. Isomeric impurities are then selectively removed by halogenation with bromine. Although high isomeric purities are claimed, the use of toxic intermediates such as dichloromethyl methyl ether and an expensive halogenating agent such as bromine make this process unsuitable for industrial utilization.

Other methods for preparing fluorinated benzaldehydes are known which use halogen-exhange (HALEX) chemistry (Journal of Fluorine Chemistry 46, 529–537 (1990). This method involves the reaction of chlorinated benzaldehydes with a metal halide, usually potassium fluoride, in a polar solvent to give a fluorinated benzaldehyde. Since only halogens in "activated" positions (those ortho and para to a formyl group) undergo halogen-exchange, the scope of this method is somewhat limited.

Aromatic formylation has traditionally been performed, since its development in the late 1800s, by a Gattermann-Koch procedure which comprises the reaction of the aromatic derivative with carbon monoxide, hydrogen chloride, and an appropriate catalyst (usually aluminum chloride). This standard reaction required the combination of equivalent amounts of aluminum chloride, carbon monoxide, and gaseous hydrogen chloride reacted in the presence of a substituted benzene. The temperature was controlled from 25 to 50° C., and the pressure was kept at 1,000 psig. Such a reaction yielded about 70% of the desired substituted benzaldehyde; however, the utilization of gaseous HCl and the need for high reaction pressures are highly undesireable from a safety standpoint. Modifications of the Gattermann-Koch reaction have been developed for specific monoalkyl-substituted benzaldehydes, such as in U.S. Pat. No. 4,622,429 to Blank et al. and di- and trialkyl-subsituted benzaldehydes in U.S. Pat. No. 4,195,040 to Renner.

While Gattermann-Koch chemistry works extremely well to prepare benzaldehyde, monoalkyl-, and polyalkyl-benzaldehydes, its use in preparing fluorinated benzaldehydes has gone virtually unexplored. Only one example is known whereby a fluorinated benzaldehyde was obtained from Gattermann-like conditions (Journal of Practical Chemistry 135, 101–127 (1932); C.A. 27, 713). In this example 3-fluoro-4-ethoxybenzaldehyde was obtained in 40% yield from the reaction of 1-fluoro-2-ethoxybenzene with zinc cyanide, hydrogen chloride, and aluminum chloride.

Even with these methods, there still remains a need in the art for methods of synthesizing fluorinated benzaldehydes in high isomeric purity and in a commercially viable manner that does not use highly toxic, corrosive, and costly reagents.

OBJECTS OF THE INVENTION

Therefore, an object of the invention is to provide a process for producing high yields of fluorinated and chlorinated benzaldehydes. A further object of the invention is to provide a highly cost-effective manner of producing such benzaldehydes which heretofore could not be produced in high yields without incurring potential problems from a safety perspective, particularly in a large scale procedure. Additionally, it is an object of this invention to provide a method of producing specific fluorinated and chlorinated benzaldehydes which requires, if at all, only a very low amount of HCl (aqueous, dry, or gaseous) in order to effectuate the necessary formylation procedure.

DETAILED DESCRIPTION OF THE INVENTION

Accordingly, this invention encompasses a method of producing a benzaldehyde of formula (I)

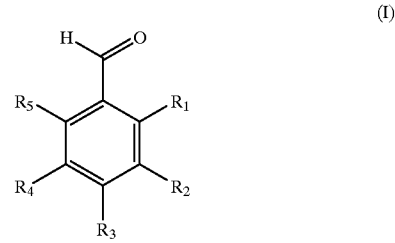

(I)

wherein $R_1$, $R_2$, $R_3$, $R_4$, and $R_5$ are selected from hydrogen, lower alkyl groups containing 1–4 carbon atoms, cycloalkyl or cycloalkylene ring systems, fluorine, chlorine; with the proviso that one and only one of $R_1$, $R_2$, $R_3$, $R_4$, and $R_5$ is fluorine or chlorine and wherein at least one of the remaining groups is a moiety other than H; which comprises contacting a substituted benzene of formula (II)

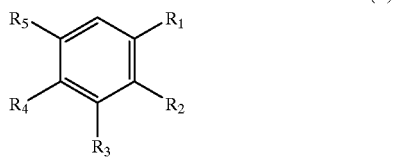

(II)

wherein $R_1$, $R_2$, $R_3$, $R_4$, and $R_5$ are selected from hydrogen, lower alkyl groups containing 1–4 carbon atoms, cycloalkyl or cycloalkylene ring systems, fluorine, chlorine; with the proviso that one and only one of $R_1$, $R_2$, $R_3$, $R_4$, and $R_5$ is fluorine or chlorine, and at least one of the other groups is a moiety other than H, in a carbon monoxide atmosphere having a pressure from about 200–800 psig, all in the presence of a metal halide, an acid selected from the group consisting of HCl, HBr, HF, HI, and mixtures thereof; wherein the acid is present in a catalytic amount of from about 0.005 to about 0.01 moles per moles of the metal halide; and wherein the reaction temperature is from about 30° to 100° C.

Any mono-halogenated benzene may be introduced within the inventive method. Specific compounds include fluorobenzene, 2-fluorotoluene, 2-chlorotoluene, 2-fluoro-m-xylene, 3-fluoro-o-xylene, 2-chloro-m-xylene, 3-chloro-o-xylene, 1-fluoro-2,3,6-trimethylbenzene and 1-chloro-2,3,6-trimethylbenzene.

The metal halide is preferably aluminum chloride, although other such halides may be utilized, such as aluminum bromide, iron (III) chloride, copper (II) chloride, zinc chloride, zirconium chloride, zirconium bromide, and the like. Also partially hydrated metal halides may be utilized as these produce acid (such as hydrochloric acid) upon dissociation within the reaction vessel, thereby providing the necessary aqueous acid component (for instance $AlCl_3 \cdot XH_2O$ wherein X is at most 1, preferably lower than 0.5, and most preferably between 0.01 and 0.1). This dissociation actually produces the requisite small, catalytic amount of aqueous hydrochloric acid without having to introduce potentially hazardous aqueous hydrochloric acid into the reaction (although an outside addition is also an available and preferred alternative). In the past variations of the Gattermann-Koch process, it was theorized that the metal halide reacted with hydrogen chloride and carbon monoxide (all in equivalent amounts) to produce a formyl cation complex which had the capability of electrophilically attacking the aromatic system. After washing with water, the metal halide was removed leaving the formylated benzene derivative. In this invention, hydrogen chloride is added, if at all, in minuscule amounts (from about 0.005 to about 0.01 moles per mole of metal halide). The metal halide is preferably present in a stoichiometric molar ratio as compared with the substituted benzene from about 1:0.75 to about 1:6, preferably from about 1:0.9 to about 1:3, and most preferably at a ratio of about 1:1. Without intending to be bound to any specific scientific theory, it is believed that such a small catalytic amount of acid (such as selected from the group consisting of HCl, HBr, HI, HF, and mixtures thereof) coupled with the metal halide produces a certain "driving amount" of the formyl cation complex. This "driving amount" thus appears to shut down the rate of possible side product formation (i.e., dimerization or polymerization, as merely examples) which have been found to occur upon utilization of standard and much larger amounts of HCl (gaseous, in particular) in past methods. Thus, it has been determined that this catalytic amount of HCl provides the necessary reaction, which ultimately forms very pure high yields of the target fluorinated and/or chlorinated benzaldehydes.

Furthermore, the utilization of very low stoichimetric amounts of hydrochloric acid is, surprisingly, highly critical to the ultimate formation of the desired substituted benzaldehydes. As noted above, it had been presumed that larger stoichiometric amounts of gaseous hydrogen chloride were necessary to form the electrophilically attacking formyl cation complex with the metal halide and the carbon monoxide as the actual reactant. It has now been found that gaseous HCl is unnecessary to produce the desired benzaldehyde (although the gaseous form is still possible in this inventive method). Also, it has been discovered that only very small catalytic amounts (as defined above) of (preferably) aqueous hydrochloric acid unexpectedly are required to form the beneficial formyl cation complex reactant in order to produce the desired substantially pure fluorinated or chlorinated benzaldehydes in high yields (although gaseous and dry forms of HCl also work). From a safety and convenience perspective, aqueous hydrochloric acid is the preferred form for this inventive method. Gaseous HCl poses a potential health hazard since control of such a gaseous state is rather difficult at times. Furthermore, dry hydrochloric acid is more difficult to handle than the liquid form. Again, however, the hydrochloric acid may be added in any form, only preferably in aqueous solution.

As discussed above, it is important to note that this acid component (such as aqueous HCl) may either be charged into the overall reaction or may be generated simply upon dissociation of the metal halide in its hydrated form. Any molarity hydrochloric acid may be used, preferably the molarity is from about 0.01 to about 12, more preferably from about 10 to 12, and most preferably about 10 (concentrated), as long as the catalytic amount (in moles) in comparison to the metal halide is met and care is taken in handling such potentially corrosive material. Without the presence of hydrochloric acid (either aqueous, gaseous, or dry), the yield of the fluorinated or chlorinated benzaldehyde is reduced; when too much hydrochloric acid is present, the reaction either generates different isomers, dimers, and/or polymers of the benzaldehyde (and thus reduces the yield and detrimentally reduces the purity of the final reaction product) or results in a reaction which produces a sludge-like solid. One further benefit of utilizing aqueous HCl with the metal halide (in particular aluminum chloride), is that, upon completion of the formylation reaction, the remaining aluminum chloride exhibits a relatively neutral pH level. Such a product cannot be used again in this process; however, such neutralized aluminum chloride can be resold for other uses (such as flocculants, anti-perspirant components, etc.). Such recycling and reuse of the compounds thus provides an environmentally friendly procedure which reduces the amount of waste to be removed and disposed of from manufacturing locations.

The carbon monoxide is introduced at a pressure of between about 100 to 800 psig, preferably from about 200 to about 600 psig, and most preferably at a pressure of about 200 psig for mono-fluorinated benzene compounds and 550 psig for chlorinated benzene compounds. Previous U.S.

Patents utilizing this methodology, U.S. Pat. Nos. 6,080,892 and 6,087,537, both to Scrivens et al., have utilized carbon monoxide pressures in the 50 to 110 psig range to achieve formylation of dialkyl-substituted benzaldehydes like o-xylene and tetralin. With the attachment of electron-withdrawing groups such as fluorine and chlorine, the benzene ring is deactivated towards attack by the formyl cation complex and thus CO pressures greater than 110 psig are needed to effect formylation of the halogenated aromatic. As illustrated by Examples 2, 3, and 5, below, the addition of an anisole derivative dramatically improves the formylation of deactivated aromatics like 2-chlorotoluene and fluorobenzene. Even in less deactivated systems such as 2-fluorotoluene, yields are improved by about 20%. Without intending to be bound to any specific scientific theory, it is believed that the anisole aluminum chloride complex acts to stabilize the formation of the formyl cation complex or produce a new more electrophilic formyl cation complex. Suitable anisole derivatives include anisole, 2-methylanisole, 3-methylanisole, 4-methylanisole, 1,2-dimethoxy benzene, 1,3-dimethoxybenzene, 1,4-dimethoxybenzene, 2,3-dimethylanisole, 2,4-dimethylanisole, 2,5-dimethylanisole,2,6-dimethylanisole, 3,4-dimethylanisole, 3,5-dimethylanisole, 2-fluoro-anisole, and the like, for this purpose.

It has also been found that the yield of the chlorinated benzaldehydes, when using HCl (preferably aqueous hydrochloric acid) in catalytic amounts, is at its peak when the reaction temperature is about 30° C. and for fluorinated benzaldehydes the reaction temperature is about 60° C. The combination of such higher temperatures with the required low stoichimetric amounts of hydrochloric acid has not been followed to produce such halogentaed benzaldehydes in the past.

An additional benefit of the inventive process lies in the possibility of omitting all solvents other than the raw materials themselves. Thus, upon reaction of 2-fluorotoluene (as merely an example), the only solvent present is the 2-fluorotoluene isomer itself. No potentially hazardous halogenated solvents or other organic liquids are required to carry out such a reaction. As a result, the final product is generally a substantially pure liquid containing all of the same compound. There is no need to undertake time-consuming and costly distillation steps to purify the resultant compounds produced by this preferred inventive method. The term "neat procedure" is herein intended and defined as this aspect. Therefore the only solvents utilized in a neat procedure are those which are raw materials within the inventive process itself. Solvents however can be used in the inventive process providing that they are more deactivated towards electrophilic formylation that the starting substrate. Preferred solvents (though not the exclusive solvents useful in this inventive process) are halogenated aromatic solvents, such as chlorotoluene, dichlorobenzene, and the like, and, as noted above, anisole and its derivatives. Such solvents may be present in amounts as low as 0.1% of the total consumption or as high as bout 99% (all by weight). Preferably, the solvent is added in an amount of from about 5 to about 50% by weight of the total weight of the reactants, more preferably from about 10 to 40%, and most preferably from about 15 to about 25%. Such a solvent has proven beneficial in aiding agitation during the reaction an in moderating the reactivity of the theorized cationic formyl catalyst within the inventive procedure. Of course, by utilizing such solvents, subsequent distilling or azeotroping must be performed to separate the residual solvent from the target benzaldehyde. Thus, the utilization of only one solvent is highly preferred in the inventive method in order to reduce the costs and time involved in manufacturing the desired fluorinated or chlorinated benzaldehyde.

PREFERRED EMBODIMENTS OF THE INVENTION

Examples of the particularly preferred inventive methods are outlined below.

EXAMPLE 1

102.13 g of aluminum chloride (mol. Wt. 133.34; 765.9 mmol) and about 497.04 g of 2-fluorotoluene (mol. Wt. 110.13; 4,513 mmol) were charged to a 2 liter Parr®-brand 4522 stainless steel reaction vessel. To this mixture was added 5 drops of concentrated HCl. The vessel was sealed, heated to 60° C., and purged three times with carbon monoxide with the pressure of the vessel increased to 200 psi for each purging. After the third purge, the vessel was vented and a final introduction of CO was made at a pressure of about 200 psi, the pressure at which the reaction was maintained for the total reaction time of about 20 hours (the reaction temperature was maintained at 60° C. for the duration as well). Once the reaction was complete, the resultant mixture (exhibiting a dark orange color) was poured into about 500 mL of ice water (which turned the solution a yellow color), to which was added 500 mL of cyclohexane. The top, organic layer was removed and washed three times with water using a separatory funnel and dried over magnesium sulfate. The residual organic phase was then distilled under vacuum to remove excess cyclohexane, 2-fluorotoluene, and left about 71.35 g of 4-fluoro-3-methylbenzaldehyde product (mol. Wt. 138.14; 516.5 mmol; yield of approximately 67.4%).

EXAMPLE 2

216.00 g of aluminum chloride (mol. Wt. 133.34; 1,619.9 mmol), 109.09 g (4-Methylanisole (mol. Wt. 122.17; 892.9 mmol), and about 522.35 g of 2-chlorotoluene (mol. Wt. 126.59; 4,126.3 mmol) were charged to a 2 liter Parr®-brand 4522 stainless steel reaction vessel. To this mixture was added 5 drops of concentrated HCl. The vessel was sealed, heated to 30° C., and purged three times with carbon monoxide with the pressure of the vessel increased to 100 psi for each purging. After the third purge, the vessel was vented and a final introduction of CO was made at a pressure of about 550 psi, the pressure at which the reaction was maintained for the total reaction time of about 66 hours (the reaction temperature was maintained at 30° C. for the duration as well). Once the reaction was complete, the resultant mixture (exhibiting a dark orange color) was poured into about 500 mL of ice water (which turned the solution a yellow color), to which was added 500 mL of cyclohexane. The top, organic layer was removed and washed three times with water using a separatory funnel and dried over magnesium sulfate. The residual organic phase was then distilled under vacuum to remove excess cyclohexane, 2-chlorotoluene, and left about 76.01 g of a benzaldehyde mixture consisting of 4-chloro-3-methylbenzaldehyde (76.5%) and 3-chloro-4-methylbenzaldehyde (23.5%) (mol.wt. 154.59; 491.7 mmol; yield of approximately 67.6%).

EXAMPLE 3

229.30 g of aluminum chloride (mol. wt. 133.34; 1,719.7 mmol), 110.0 g (4-Methylanisole (mol. Wt. 122.17; 900.4 mmol), and about 500 g of 2-fluorotoluene (mol. Wt. 110.13; 4,540.1 mmol) were charged to a 2 liter Parr®-brand 4522 stainless steel reaction vessel. To this mixture was added 5 drops of concentrated HCl. The vessel was sealed, heated to 30° C., and purged three times with carbon monoxide with the pressure of the vessel increased to 100 psi for each purging. After the third purge, the vessel was vented and a final introduction of CO was made at a pressure of about 550 psi, the pressure at which the reaction was maintained for the total reaction time of about 66 hours (the reaction temperature was maintained at 30° C. for the duration as well). Once the reaction was complete, the resultant mixture (exhibiting a greenish-brown color) was poured into about 500 mL of ice water (which turned the solution a yellow color), to which was added 500 mL of cyclohexane. The top, organic layer was removed and washed three times with water using a separatory funnel and dried over magnesium sulfate. The residual organic phase was then distilled under vacuum to remove excess cyclohexane, 2-fluorotoluene, and left about 98.01 g of 4-fluoro-3-methylbenzaldehyde product (mol. Wt. 138.14; 709.5 mmol; yield of approximately 86.7%). The 4-fluoro-3-methylbenzaldehyde product may then be easily separated from any residual 4-methylanisole by conversion into its corresponding bisulfite adduct, filtration, and decomposition of the bisulfite adduct under acidic or basic conditions.

EXAMPLE 4

100.89 g of aluminum chloride (mol. Wt. 133.34; 756.6 mmol) and about 503.54 g of 3-fluorotoluene (mol. Wt. 110.13; 4,572 mmol) were charged to a 2 liter Parr®-brand 4522 stainless steel reaction vessel. To this mixture was added 5 drops of concentrated HCl. The vessel was sealed, heated to 60° C., and purged three times with carbon monoxide with the pressure of the vessel increased to 200 psi for each purging. After the third purge, the vessel was vented and a final introduction of CO was made at a pressure of about 200 psi, the pressure at which the reaction was maintained for the total reaction time of about 17 hours (the reaction temperature was maintained at 60° C. for the duration as well). Once the reaction was complete, the resultant mixture (exhibiting a dark orange color) was poured into about 500 mL of ice water (which turned the solution a yellow color), to which was added 500 mL of cyclohexane. The top, organic layer was removed and washed three times with water using a separatory funnel and dried over magnesium sulfate. The residual organic phase was then distilled under vacuum to remove excess cyclohexane, 3-fluorotoluene, and left about 79.65 g of a benzaldehyde mixture consisting of 4-fluoro-2-methylbenzaldehyde (88.4%) and 2-fluoro-4-methylbenzaldehyde (11.6%) (mol. Wt. 138.14; 576.6 mmol; yield of approximately 76.2%).

EXAMPLE 5

62.4 g of aluminum chloride (mol. Wt. 133.34; 468.0 mmol), 450.0 g of 1,2-dichlorobenzene (mol. Wt. 147.00; 3,061 mmol), and about 48.00 g of 2-fluoro-m-xylene (mol. Wt. 124.16; 386.6 mmol) were charged to a 2 liter Parr®-brand 4522 stainless steel reaction vessel. To this mixture was added 5 drops of concentrated HCl. The vessel was sealed, heated to 50° C., and purged three times with carbon monoxide with the pressure of the vessel increased to 100 psi for each purging. After the third purge, the vessel was vented and a final introduction of CO was made at a pressure of about 200 psi, the pressure at which the reaction was maintained for the total reaction time of about 16 hours (the reaction temperature was maintained at 50° C. for the duration as well). Once the reaction was complete, the resultant mixture (exhibiting a dark orange color) was poured into about 500 mL of ice water (which turned the solution a yellow color), to which was added 500 mL of cyclohexane. The top, organic layer was removed and washed three times with water using a separatory funnel and dried over magnesium sulfate. The residual organic phase was then distilled under vacuum to remove excess cyclohexane, 2-fluoro-m-xylene, 1,2-dichlorobenzene, and left about 40.39 g of a benzaldehyde mixture consisting of 4-fluoro-3,5-dimethylbenzaldehyde (73.8%) and 3-fluoro-2,4-dimethylbenzaldehyde (26.2%) (mol. Wt. 152.17; 265.4 mmol; yield of approximately 68.6%).

EXAMPLE 6

67.60 g of aluminum chloride (mol. Wt. 133.34; 507.0 mmol), 450.0 g of 1,2-dichlorobenzene (mol. Wt. 147.00; 3,061 mmol), and about 503.54 g of 3-fluoro-o-xylene (mol. Wt. 124.16; 789.3 mmol) were charged to a 2 liter Parr®-brand 4522 stainless steel reaction vessel. To this mixture was added 5 drops of concentrated HCl. The vessel was sealed, heated to 50° C., and purged three times with carbon monoxide with the pressure of the vessel increased to 100 psi for each purging. After the third purge, the vessel was vented and a final introduction of CO was made at a pressure of about 200 psi, the pressure at which the reaction was maintained for the total reaction time of about 28 hours (the reaction temperature was maintained at 50° C. for the duration as well). Once the reaction was complete, the resultant mixture (exhibiting a dark orange color) was poured into about 500 mL of ice water (which turned the solution a yellow color), to which was added 500 mL of cyclohexane. The top, organic layer was removed and washed three times with water using a separatory funnel and dried over magnesium sulfate. The residual organic phase was then distilled under vacuum to remove excess cyclohexane, 3-fluoro-o-xylene, 1,2-dichlorobenzene, and left about 94.98 g of a benzaldehyde mixture consisting of 4-fluoro-2,3-dimethylbenzaldehyde (89.1%) and 2-fluoro-3,4-dimethylbenzaldehyde (10.9%) (mol. Wt. 152.17; 624.2 mmol; yield of approximately 79.1 %).

While specific features of the invention have been described, it will be understood, of course, that the invention is not limited to any particular configuration or practice since modification may well be made and other embodiments of the principals of the invention will no doubt occur to those skilled in the art to which the invention pertains. Therefore, it is contemplated by the appended claims to cover any such modifications as incorporate the features of the invention within the true meaning, spirit, and scope of such claims.

That which is claimed is:

1. A benzaldehyde of the formula (I)

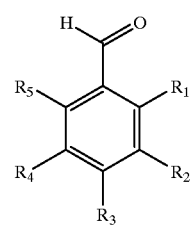

wherein $R_1$, $R_2$, $R_3$, $R_4$, and $R_5$ are selected from hydrogen, lower alkyl groups containing 1–4 carbon atoms, cycloalkyl or cycloalkylene ring systems, fluorine, chlorine; with the proviso that one and only one of $R_1$, $R_2$, $R_3$, $R_4$, and $R_5$ is Fluorine or Cl and wherein at least one of the remaining groups is a moiety other than H; wherein if $R_3$ is fluorine, at least one of $R_1$ and $R_5$ must be a moiety other than H.

2. The compound of claim 1 wherein $R_3$ is Cl and $R_4$ is lower alkyl.

3. The compound of claim 2 wherein said lower alkyl is methyl.

4. The compound of claim 1 wherein $R_4$ is Cl and $R_3$ is lower alkyl.

5. The compound of claim 4 wherein said lower alkyl is methyl.

6. The compound of claim 1 wherein one of $R_1$ and $R_5$ is Fl and $R_3$ is lower alkyl.

7. The compound of claim 6 wherein said lower alkyl is methyl.

8. The compound of claim 1 wherein $R_3$ is F and both of $R_2$ and $R_4$ are lower alkyl.

9. The compound of claim 8 wherein said lower alkyl is methyl.

10. The compound of claim 1 wherein one of $R_1$ and $R_5$ is lower alkyl, $R_3$ is lower alkyl and one of $R_2$ and $R_4$ is F.

11. The compound of claim 10 wherein said lower alkyl is methyl.

12. The compound of claim 1 wherein one of $R_1$ and $R_5$ is lower alkyl, one of $R_2$ and $R_4$ is lower alkyl, and $R_3$ is F.

13. The compound of claim 12 wherein said lower alkyl is methyl.

14. The compound of claim 1 wherein one of $R_1$ and $R_5$ is F, $R_3$ is lower alkyl, and one of $R_2$ and $R_4$ is lower alkyl.

15. The compound of claim 14 wherein said lower alkyl group is methyl.

16. The compound of claim 1 wherein one of $R_1$ and $R_5$ is lower alkyl and $R_3$ is F.

17. The compound of claim 16 wherein said lower alkyl is methyl.

\* \* \* \* \*

UNITED STATES PATENT AND TRADEMARK OFFICE
CERTIFICATE OF CORRECTION

PATENT NO. : 6,297,405 B1
DATED : October 2, 2001
INVENTOR(S) : John David Anderson and Walter Scrivens It is certified that error appears in the above-identified patent and that said Letters Patent is hereby corrected as shown below:

<u>Column 9,</u>
Line 4, delete "F1" and insert -- fluorine --.

Signed and Sealed this

Twenty-sixth Day of July, 2005

JON W. DUDAS
*Director of the United States Patent and Trademark Office*